United States Patent
Tankovich

Patent Number: 6,152,917
Date of Patent: *Nov. 28, 2000

[54] HAIR REMOVAL DEVICE

[75] Inventor: Nikolai I. Tankovich, San Diego, Calif.

[73] Assignee: ThermoLase Corporation, San Diego, Calif.

[*] Notice: This patent is subject to a terminal disclaimer.

[21] Appl. No.: 08/994,039

[22] Filed: Dec. 18, 1997

Related U.S. Application Data

[62] Division of application No. 08/777,576, Dec. 31, 1996, which is a continuation of application No. 08/468,022, Jun. 6, 1995, abandoned, which is a division of application No. 08/005,810, Jan. 19, 1993, Pat. No. 5,425,728, which is a continuation-in-part of application No. 07/783,789, Oct. 29, 1991, Pat. No. 5,226,907.

[51] Int. Cl.[7] ............................. A61B 17/36; A45D 26/00
[52] U.S. Cl. ............................. 606/9; 606/133; 606/131
[58] Field of Search .................................. 606/9, 10, 11, 606/12, 14, 15, 16, 17, 131, 133

[56] References Cited

U.S. PATENT DOCUMENTS

| | | |
|---|---|---|
| 3,495,962 | 2/1970 | Norton et al. . |
| 3,538,919 | 11/1970 | Mayer . |
| 3,693,623 | 9/1972 | Harte et al. . |
| 3,769,963 | 11/1973 | Goldman et al. . |
| 3,794,028 | 2/1974 | Mueller et al. . |
| 3,834,391 | 9/1974 | Block . |
| 3,900,034 | 8/1975 | Katz et al. . |
| 4,336,809 | 6/1982 | Clark . |
| 4,388,924 | 6/1983 | Weisman er al. . |
| 4,434,064 | 2/1984 | Chao et al. . |
| 4,461,294 | 7/1984 | Baron . |
| 4,608,978 | 9/1986 | Rohr . |
| 4,617,926 | 10/1986 | Sutton . |
| 4,712,543 | 12/1987 | Baron . |
| 4,813,412 | 3/1989 | Yamazaki . |
| 5,059,192 | 10/1991 | Zaias . |
| 5,226,907 | 7/1993 | Tankovich ............................. 606/133 |
| 5,425,728 | 6/1995 | Tankovich ............................. 606/9 |
| 5,647,866 | 7/1997 | Zaias et al. ............................. 606/9 |
| 5,752,948 | 5/1998 | Tankovich et al. ..................... 606/9 |
| 5,752,949 | 5/1998 | Tankovich et al. ..................... 606/9 |

FOREIGN PATENT DOCUMENTS

| | | |
|---|---|---|
| 1041610 | 6/1974 | Canada . |
| 1208702 | 7/1986 | Canada . |
| 0 649 667 A2 | 4/1995 | European Pat. Off. . |
| 2267122 | 4/1975 | France . |
| 2595239 | 6/1982 | France . |
| 2590791 | 6/1987 | France . |
| 2515697 | of 0000 | Germany . |
| 32209g2 | 6/1982 | Germany . |
| 63-249577 | 10/1988 | Japan . |
| 1 288 805 | 9/1972 | United Kingdom . |
| 8002640 | 12/1980 | WIPO . |
| WO 85/05021 | 11/1985 | WIPO . |
| 8602783 | 5/1986 | WIPO . |
| WO 90/11797 | 10/1990 | WIPO . |
| 9104073 | 4/1991 | WIPO . |
| WO 91/13652 | 9/1991 | WIPO . |
| WO 91/13653 | 9/1991 | WIPO . |
| WO 93/21842 | 11/1993 | WIPO . |
| WO 93/21992 | 11/1993 | WIPO . |

OTHER PUBLICATIONS

Porphyrins in Tumor Phototherapy–Andereoni 143–155 (1984).
A. Anders, et al., Investigation and Therapy in Dermatology, Conf. Laser 77 Optics–Electronics 20–24 (Jun. 1977).

*Primary Examiner*—Max Hindenburg
*Assistant Examiner*—Sonya Harris-Ogugua
*Attorney, Agent, or Firm*—Fish & Richardson P.C.

[57] ABSTRACT

A device for inhibiting growth of unwanted hair. A light-absorbing contaminant applied to the surface of a section of skin so that some of the contaminant infiltrates hair ducts is placed in spaced apart relationship to an illumination source that provides light absorbed by the contaminant. When the light penetrates the section of skin and is absorbed by the contaminant in the hair ducts, the follicles and/or skin tissue surrounding the follicles is heated so as to inhibit hair growth.

24 Claims, 5 Drawing Sheets

HAIR REMOVAL DEVICE

This application is a divisional of copending U.S. application Ser. No. 08/777,576, filed Dec. 31, 1996, which is a continuation of U.S. application Ser. No. 08/468,022, filed Jun. 6, 1995 and now abandoned, which is a divisional of U.S. application Ser. No. 08/005,810, filed Jan. 19, 1993 and now issued as U.S. Pat. No. 5,425,728, which is a continuation-in-part of U.S. application Ser. No. 07/783,789, filed Oct. 29, 1991 and now issued as U.S. Pat. No. 5,226,907.

BACKGROUND OF THE INVENTION

The principal methods presently used for hair removal involve the use of electrolysis techniques or chemical depilatories. These techniques involve some pain, are time consuming, and demand a fair degree of expertise in their application and normally do not guarantee a permanent effect.

Laser use in medicine is well known. For example, lasers are used in surgery for both cutting and cauterization. Lasers have been used for many years for removing tattoos under the surface of the skin. In this case a laser beam penetrates the skin and is absorbed by and destroys the ink particle. A similar procedure has been used for years to remove birth marks where the laser is matched to an absorption peak of the erythrocyte's hemoglobin in the tiny capillaries under the skin to destroy the capillaries.

The prior art of hair removal also includes attempts at removing hair with laser beams. Three such techniques are described in the following United States patents: Weissman et al., Method for Laser Depilation Device and Method, U.S. Pat. No. 4, 388,924; Sutton, Depilation Device and Method, U.S. Pat. No. 4,617,926; and Mayer, Depilation by Means of Laser Energy, U.S. Pat. No. 3,538,919. All of these devices and methods teach the removal of hairs one hair at a time with a narrowly focused laser beam. Therefore, they are relatively inefficient and time consuming. A recent patent by Zaias, U.S. Pat. No. 5,059,192 issued Oct. 22, 1991 discloses a process for using a laser beam matched to the melanin found at the base of the hair follicle and papilla.

It has been known for at least 20 years in the medical profession that selective absorption of laser radiation can sometimes be enhanced by the technique of staining pathological tissues with various vital dyes. (See Goldman U.S. Pat. No. 3,769,963.)

What is needed is a simple, harmless device and method for removal of hair over a relatively broad area of skin.

SUMMARY OF THE INVENTION

Present invention provides a device and process for the permanent removal of unwanted human hair. The hair or the skin tissue feeding or surrounding the hair on a section of skin is contaminated with a substance having high absorption of a frequency band of light. The section of skin is illuminated with light at this frequency band at sufficient intensity and duration to destroy the follicle or the skin tissue feeding the hair. Specific embodiments destroy the follicle or the tissue by heating or by photochemical reaction.

DETAILED DESCRIPTION OF PREFERRED EMBODIMENTS

Preferred embodiments of the present invention can be described by reference to the Figures.

COAT AND HEAT METHOD

Skin Preparation

Figure 1:
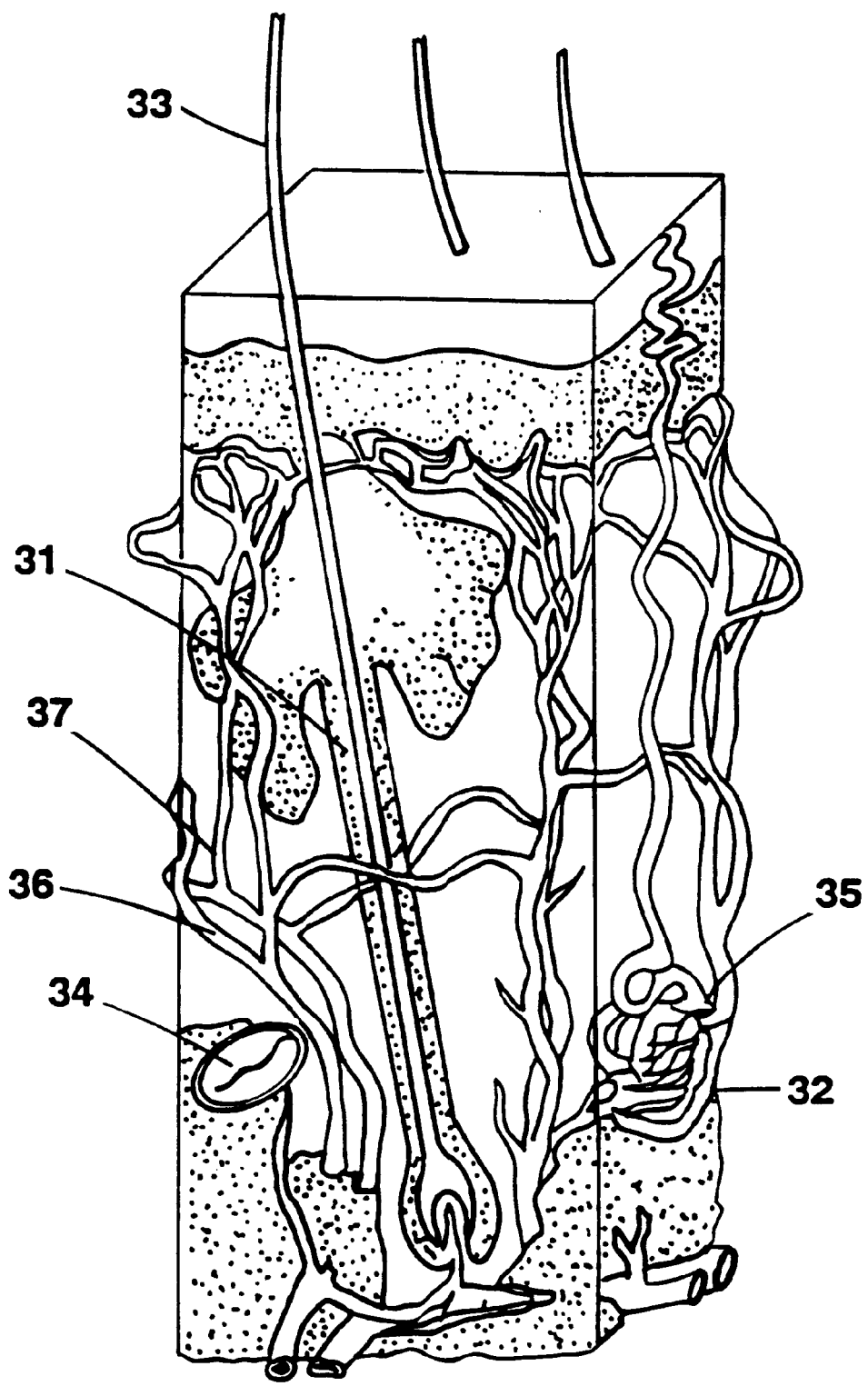
FIG. 1 is a drawing of a cross section of human skin showing a growing hair.

A section of human skin with a cross section of one hair is shown in FIG. 1. A first preferred embodiment of the present invention can be described by reference to FIGS. 2–4. FIG. 1 shows the hair shaft 33, a nerve ending 34, a sweat gland 35, arteries 36, and veins 37. First, a laser absorbing carbon suspension is prepared of carbon powder in peach oil. The particle size of the powder preferably is about 10–20 nm, and the concentration of the particles in the suspension preferably is about 15% to 20% by volume.

Figure 2A:
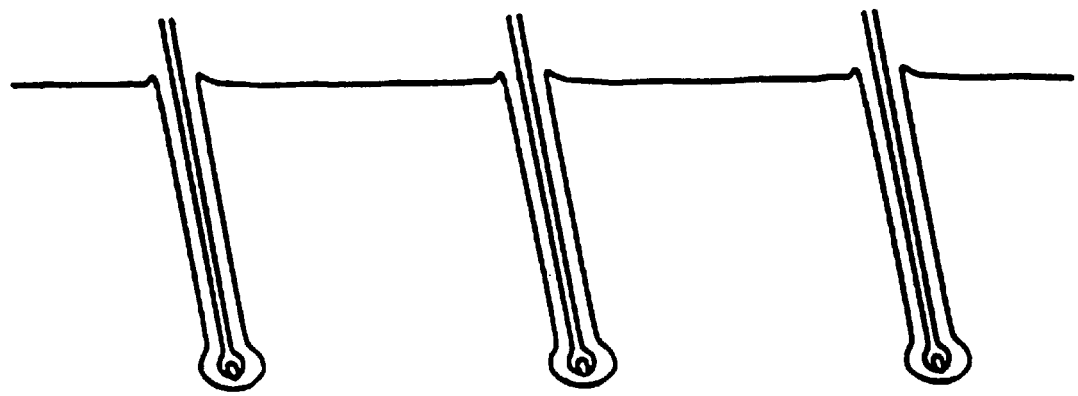
FIGS. 2A, B and C show a cross section of skin and three hairs during three stages of a process of one embodiment of the present invention.
Figure 2B:
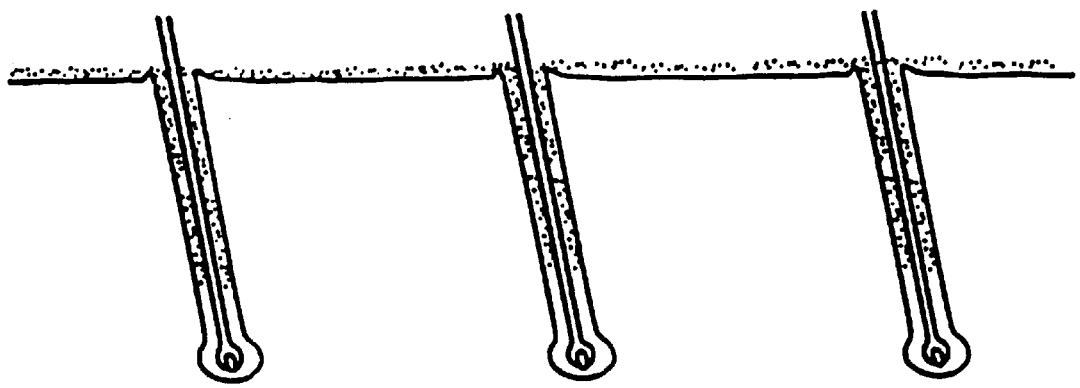
Figure 2C:
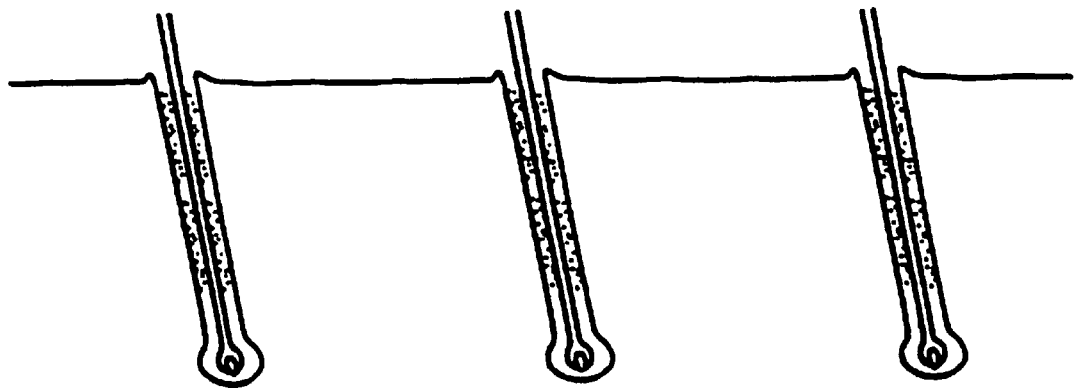

A clean section of skin is depicted in FIG. 2A. The suspension described above is rubbed on the skin with a massaging action so that portion of the carbon suspension infiltrates the hair ducts of the hairs that are to be removed as shown in FIG. 2B. Ultrasound applied to the skin surface with frequencies in the range of about 3.5 to about 10 MHz at a power level of about 0.1 to 0.2 Watt with for about four to five minutes can be used to help force the suspension into the ducts. Next, the surface of the skin is cleaned, preferably with an alcohol pad, so as to make the skin surface clean, but to leave the hair pores contaminated with the carbon suspension as shown in FIG. 2C.

Laser Application

The laser device used in this preferred embodiment is a $CO_2$ pulse laser which has energy spikes in the wavelength range of about 10.6 microns. Light in this wavelength range will pass through the outer layer of the surface of the skin and is readily absorbed in carbon. Laser parameters, such as a pulse width and repetition rate, can be selected to best fit the skin and hair types of the patients. The parameters for two specific examples that have been utilized with good results for hair removal are shown in Table 1:

TABLE 1

| | Parameters Preferred. | |
|---|---|---|
| | First Example | Second Example |
| Pulse Width | 275 ns | 200 ns |
| Repetition Rate | 30 Hz | 8 Hz |
| Laser Spot Size | 1 cm$^2$ | 1 cm$^2$ |
| Energy per Pulse | 0.1 Joule | 0.2 Joule |
| Scanning Rate | 20 seconds per 10 cm$^2$ | 30 seconds per 10 cm$^2$ |

Each point on the skin receives illumination for about 2 seconds and each square centimeter receives about 6 Joule-sof energy. Some of the light is reflected. Of the light which is not reflected, a significant portion of the energy of each pulse is absorbed in the carbon.

Figure 3:
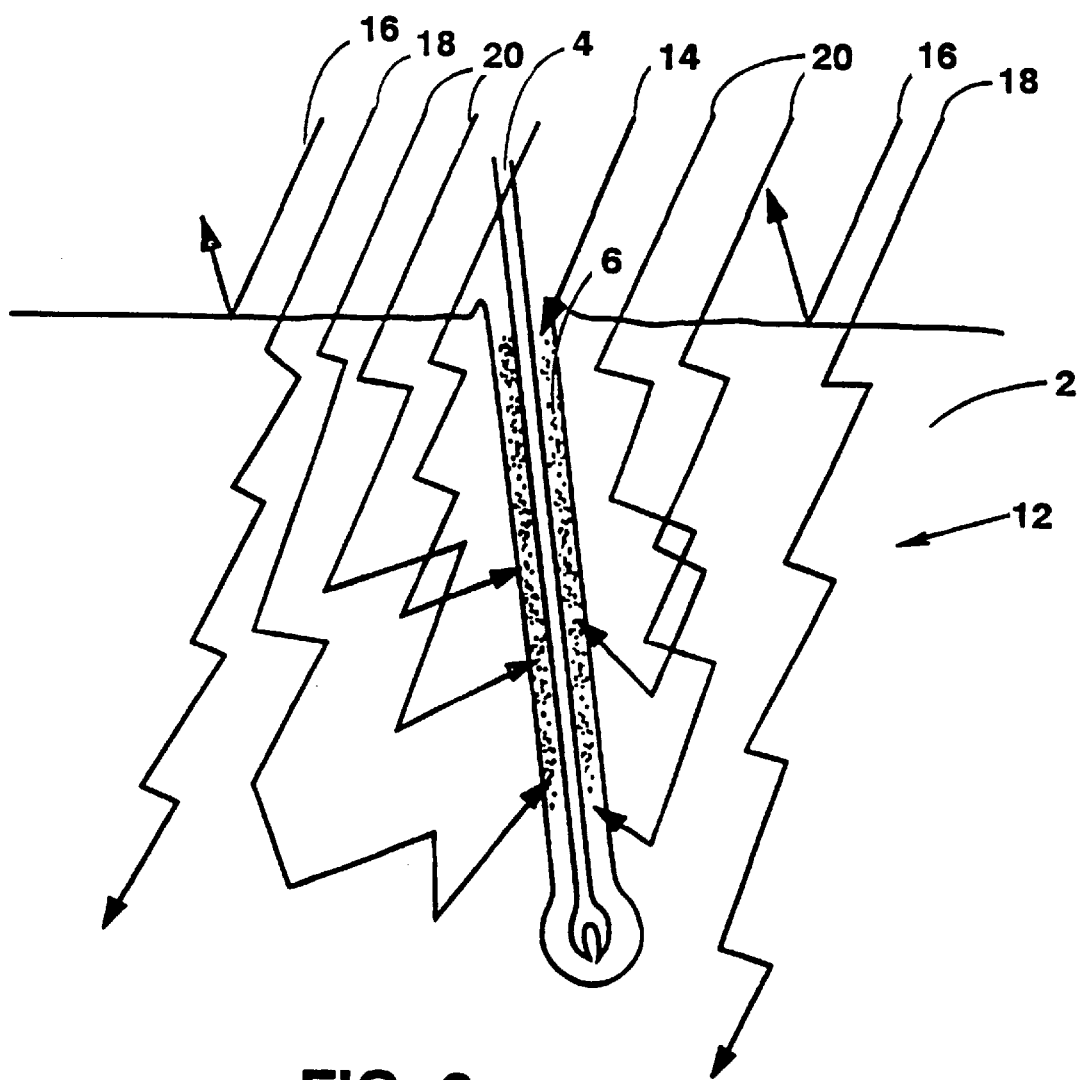
FIG. 3 shows qualitatively the paths of the photons of a laser pulse with absorption of photons in a carbon-oil suspension.

FIG. 3 shows a simplified view of a section of human skin and shows qualitatively the paths 12 of some of the photons of a laser pulse illuminating a section of skin 2 containing a hair duct with a hair 4 contaminated with carbon suspension 6. A few of the photons travel directly through the skin and are absorbed in the carbon (depicted by photon 14). Some are reflected from the skin surface (depicted by photons 16). Some are absorbed in the skin (depicted as photons 18) and a portion of the photons (depicted as photons 20) is absorbed in the carbon.

Operating within the parameters specified is important. The parameters are chosen to preferentially heat the carbon suspension, which in turn raises the temperature of the hair follicles and the blood vessels feeding the follicles high enough to destroy the hair follicles and/or the tissue feeding the follicles, while heat to the rest of the skin tissue is minimized. The time of energy application is a most important parameter. It must be chosen so that a large amount of energy is deposited in the suspension quickly, so that the temperature of the suspension rises rapidly to about 70° C.–80° C., or above. This temperature applied for about 1 second is enough to kill the follicles and/or the vessels feeding the follicles. During this short period, heat transferred to the skin tissue is not enough to damage the skin tissue, except that tissue immediately surrounding the follicle. It is good practice is to start out with the power densities specified. It will be evident when enough energy is being supplied because the hair shaft will begin to curl. If curling is not achieved, the power density could be increased up to about 2–3 Joules per square centimeter, or until sufficient energy is delivered to devitalize the hair.

Hair removal experiments have been performed using the parameters shown in Table 1 with excellent results. There is no significant pain, yet hair is permanently removed and there is no apparent detrimental effect. A qualitative mathematical analysis was performed in order to estimate heat absorption and temperature distribution in the hair and skin tissue. This analysis is shown in Table 2 below.

TABLE 2

Heating of hair and carbon oil suspension in a hair duct

| | |
|---|---|
| Repetition Rate | 33 pulses per second |
| Time between pulses | about 0.03 seconds |
| Hair duct diameter | 0.1 mm |
| Energy per Pulse | 0.1 J |
| Energy per second | (0.1 J) (33) = 33 J/sec = 3 W |
| Beam spot | 1 cm$^2$ |
| Hair spacing | 130 hairs/cm$^2$ |
| Distance between hairs | 0.1 cm = 1 mm |
| Assume 1/4 of energy goes into hair duct | |
| Energy per hair per pulse | (0.1 J/130)/4 = 0.00016 J |
| Volume of hair duct | |
| Length | 1 mm |
| Diameter | 0.1 mm |
| Vol. = $\pi l (D/2)^2$ = | (0.1 cm) $\pi$ (f(0.01/2))$^2$ = 0.0000078 cm$^3$ |
| Density of oil and hair = | 0.9 gm/cm$^3$ |
| Mass of oil & hair | 0.000007 gm |
| Specific heat of oil & hair assume | 4 J/gm ° C. |
| Temperature rise per pulse, $\Delta T = (Q/mc)$ | (0.00016 J/(0.000007 gm) 4 J/ gm ° C.) = 5° C. |

Thus, under the assumptions in Table 2, each pulse would heat the carbon oil suspension roughly about 5° C. (The reader is cautioned that the above analysis is not to be relied on as a quantitative description of the process of heating the carbon oil suspension in the hair duct. For example, for many people the assumption that one-fourth of the energy of each pulse goes into the hair duct is probably too high.)

Each pulse will also heat the skin in general. A good estimate is not available of what portion of the pulse energy is reflected, absorbed in the hair ducts, and absorbed in the skin in general. However, for this qualitative analysis it is assumed that about one-half of the energy of the laser pulse reflects, one-quarter is absorbed in the hair ducts, and one-quarter is absorbed in the skin in general. If it is assumed that the skin is heated fairly uniformly to a depth of 0.2 cm, that the skin density is 1 gm/cm$^3$, and the specific heat for skin is 4 J/gm° C., the 0.025 J pulse will heat this typical skin section about 0.04 degrees C. Based on these assumptions, 60 pulses over about 2 seconds will give a general heating of about 2° C. Therefore, heat deposited generally to the skin would be negligible. This analysis is only qualitative in nature. In practice, it is believed that much of the energy from the pulse $CO_2$ laser is absorbed in a very thin area of the surface, possibly as thin as 0.1 mm depending on the dryness of the skin. In some cases a very thin layer of the skin is actually vaporized in the process, but this layer usually consists of essentially dead cells that would naturally flake off the skin surface. Also, since the epidermis is such a poor heat conductor, the underlying layers of skin are typically protected from damage, except those portions very close to the carbon-oil suspension.)

However, heat from the hot carbon-oil suspension will be transferred by conduction to the tissue surrounding the hair duct. The following relationship (see note 10 of Zwig & Wibber, "Mechanical and Thermal Parameters In Pulsed Laser Cutting of Tissue," *IEEE Journal of Quantum Electronics,* Vol. QE-23, No. 10 Oct. (1987),) was used to estimate the heat spread from the hot carbon oil suspension in the duct:

$$\delta = \sqrt{K\tau}$$

where $\delta$ represents the thickness of a heated zone during a time $\tau$, K being the heat of conduction. Assuming K=1.44× 10$^{-3}$ cm$^2$/sec and using 0.03 sec as the time interval between pulses, the heat spreads out an estimated 0.007 cm from the hair duct between each pulse. This is about equal to the radius of the hair duct. It is assumed, therefore, that about one-half of the temperature rise from each pulse is transferred to the surrounding tissue during the 0.0.3 second following each pulse. This means that the net increase in the temperature of the carbon-oil suspension from each pulse will be roughly 2.5° C.

Figure 4A:
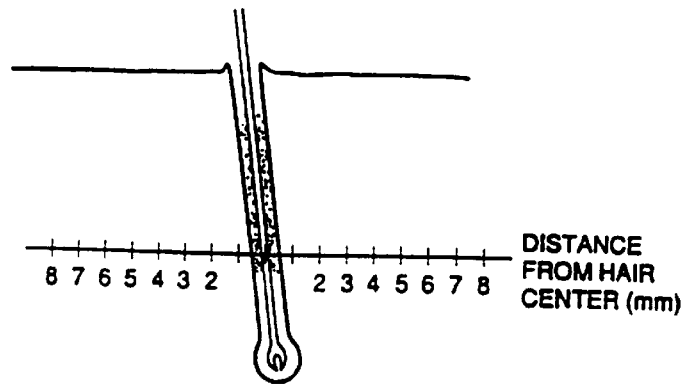
FIGS. 4A and B show the temperature distribution near a typical hair during the process of a preferred embodiment of the present invention.
Figure 4B:
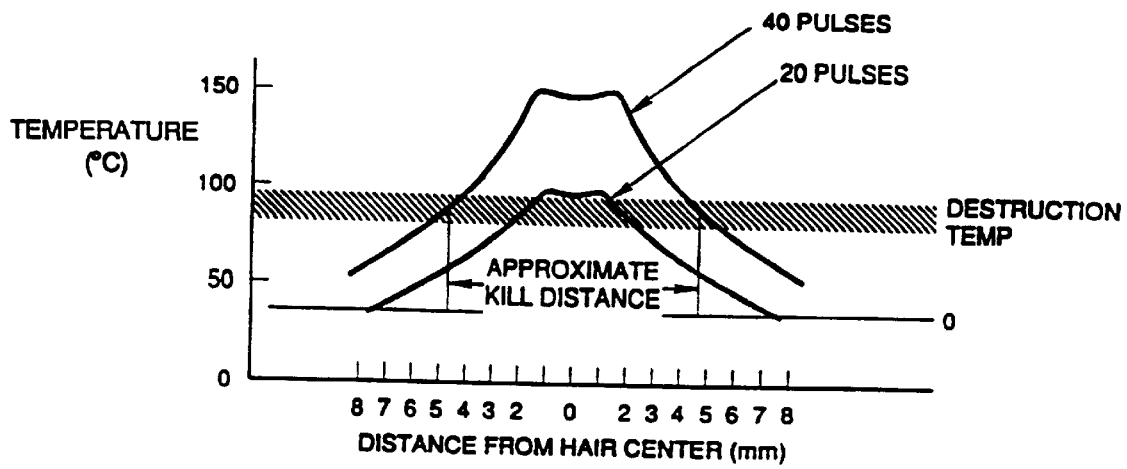

Thus, as depicted in FIG. 4, in about two-thirds of a second the temperature of the carbon-oil suspension in the hair duct has risen from a normal temperature of 37° C. to about 90° C., a temperature high enough to destroy the follicle and the tissue cells immediately surrounding the hair follicle (i.e., within about ±5 hair diameter). In a little more than one second the temperature has risen to about 140° C., which is the upper end of the safe range. At this point the patient would begin to feel pain. Therefore, the illumination should be applied so that no spot is illuminated longer than about one or two seconds during one scan. FIGS. 4A and 4B show a rough approximation of the temperature distribution between ±8 millimeters from the center for a typical hair duct after 20 and 40 pulses, respectively.

For this process, a 10 cm$^2$ area is illuminated by making 2 or 3 passes over each spot during a 20 second scanning period. For each spot the temperature will have dropped from the high point of about 100° C.–140° C. to below about 50° C. during the approximately 7 seconds between scans.

As a result of the illumination, it is estimated that for many patients essentially all follicles will be devitalized or will become so within about 2 weeks because of reduced nourishment due to the destruction of the tissue surrounding the hair duct. The destroyed tissue is estimated to be confined to within about 3–6 millimeters (about 6–12 hair diameters) from the center of the hair. Although preferred for some persons, this embodiment does not work well on all persons. In some cases pain and some surface burning is experienced before the hair tissue is destroyed. For these persons, one of the alternative embodiments is recommended.

NEAR INFRARED LASER METHOD

This process is the same as the first embodiment described above except the wavelength of the laser is 1.06 microns, the pulse duration is about 1000 times less (i.e, in the range of 25–30 pico seconds), the energy per pulse is about 100 times less (or about 3–6 mJ) and the spot size is about 0.1 to 0.3 $cm^2$. At this wavelength, the skin penetration is maximum. In this embodiment much less energy is required because a much larger percentage of the energy is absorbed in the contaminant.

STAIN METHOD

Figure 5:
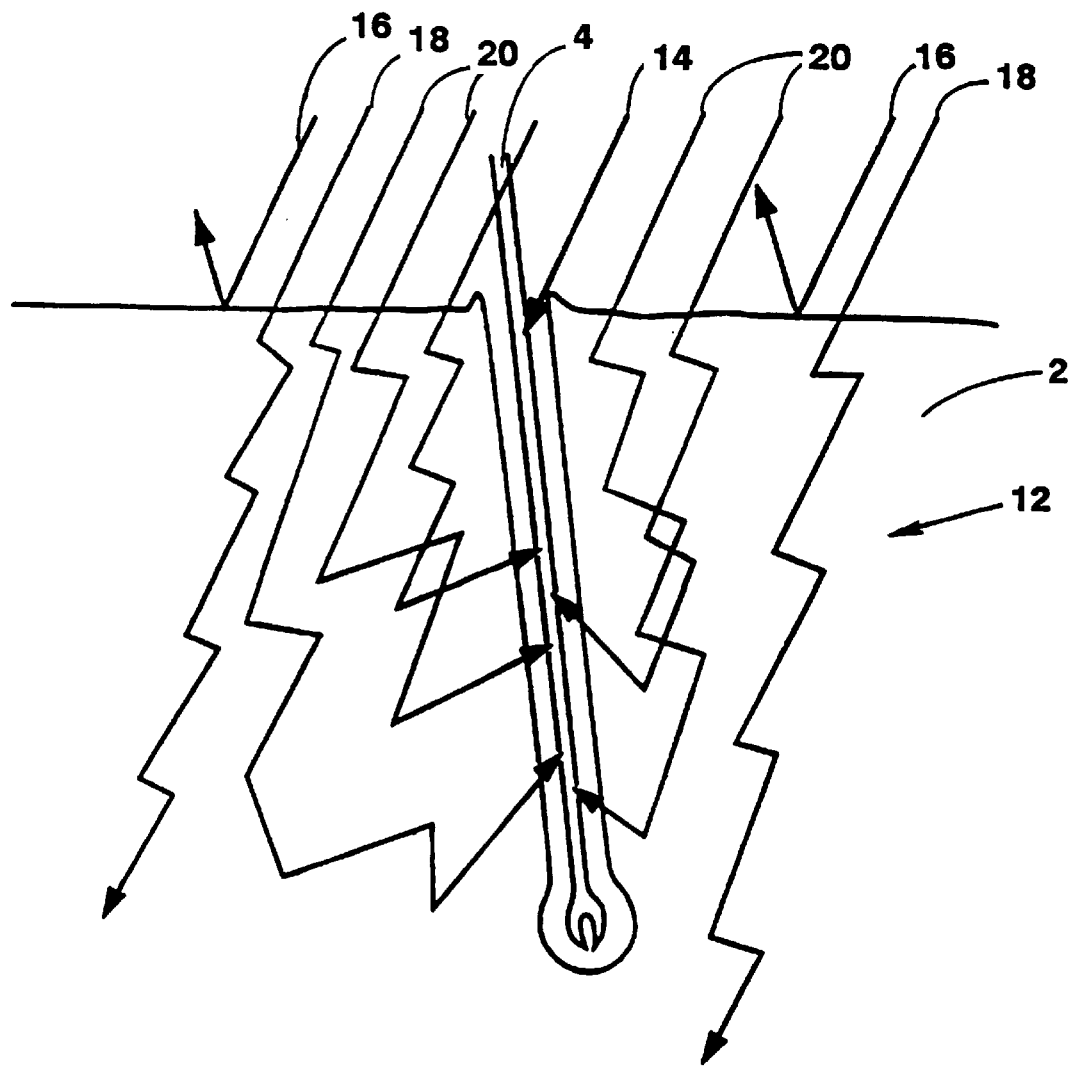
FIG. 5 shows qualitatively the paths of the photons of a laser pulse with photon absorption in hair dye.

A second embodiment involves the use of dyes to stain the hair follicles. A pulse laser beam of light having a wavelength corresponding precisely to a resonance frequency of the dye is used to illuminate the hair and skin area where the hair is to be removed. The dye and laser beam are chosen so that there is very little absorption by the skin tissue, but great absorption by the dye. As indicated in FIG. 5 the photons will undergo diffuse reflection in the skin. But when a photon intersects the hair, it is absorbed.

To stain the follicles, dye is mixed to form a solution that will penetrate into the follicles. A good substance used to form this solution is hydropertis. In one embodiment, commercial hair dye #124 (deep black with blue) and/or India ink, which already comprises such a solution, is used. The dye solution is rubbed on the skin and hair and let stand for 30 minutes. The dye will migrate through the hair all the way to the root. India ink alone could also be used.

The skin is cleaned using a standard dye removal solution. India ink and dye #124 have absorption peaks for light at wavelengths of about 694 nm and 587 nm, which match perfectly with the output of a 587 nm wavelength dye laser. Dye #124 also has a resonance peaks for light at wavelengths of about 531 and 584 nm, corresponding to the output of a copper vapor laser supplied by Spectra Physics.

In another embodiment, a ruby laser with a pulse width of 150 ns and 200 μs dye laser can be used. With a beam having a cross-sectional diameter of 0.4 cm, the energy density is about 2.5–8.5 $J/cm^2$. Many other dye-laser combinations known to persons skilled in the laser arts can also be used in this invention. The secret is to match the laser wavelength with a resonance peak in a dye that can be applied to and absorbed in the follicles. India ink essentially the same as tattoo ink) has a high absorption in the range from UV up to IR.

Described below is a good general procedure for utilizing a stain in a hair removal procedure.

1. Discolor hairs with hydroperoxide 1 hour prior to staining hairs.
2. Cut or shave hairs leaving about 1 mm of hair above the skin.
3. Stain hairs with the ink or dye (red or orange, preferably). More ink or dye would be located around the hair and its pores because of the liquid surface tension near the hair.
4. Leave the stained area covered for 40–50 minutes.
5. Wash skin surface several times with alcohol, until the skin surface returns to its normal color, except the hair pores.
6. Make 3–4 test spots with different power densities to choose an individual optimal dose for the patient.
7. Start lasering in 3–6 hours after the staining procedure, one laser shot per spot.
8. Cover the area irradiated with Aloe Vera Gel or Laser Cream after the procedure.
9. Give these instructions to the patient:
   use Bicicytrine ointment topically for the first three days post lasing;
   spare the area irradiated when taking shower, don't use hard sponges;
   protect the area from direct sunlight by sunscreen or dress;
   take Tylenol® if there is any discomfort;
   call if necessary.
10. Examine the skin in 1, 2 and 3 weeks.
11. Repeat the procedure if necessary for the hairs which were in Anlagen or Catagen phases during the laser HR.

A titanium-sapphire laser can also be used. This laser covers the parameters of the Ruby laser, penetrates human skin about as well as the Ruby laser, and has a wider band of radiation within the absorption spectrum of these dyes.

PHOTO CHEMICAL DESTRUCTION

A third embodiment for practicing this invention is to apply a photosensitizer to the hair so that it is absorbed along the full length of the hair to the root. The skin area is then illuminated with laser light that readily penetrates the skin, but is absorbed resonantly by the photosensitizer so that the photosensitizer undergoes a chemical reaction that is deadly to the hair follicles.

A good specific example of this embodiment of the present invention is to apply a 20% solution of one or more hematoporphyrin derivative topically to the skin over and area where the hair to be removed has been recently shaved. The solution is absorbed into the portion of the hair remaining under the skin by capillary action. The skin is then cleaned thoroughly with an alcohol pad. Next the skin area is illuminated with an argon dye laser at about 632 nm. The energy required is about 5–10 Joules per square centimeter. In this case, the time period is not very important. It could be several minutes per square centimeter. When the laser energy is absorbed in an hematoporphyrin derivative, singlet oxygen is produced as a result of photochemical reaction. The singlet oxygen is toxic for protein and phospholipids in the hair follicles, and the follicles are thus killed.

SKIN COVER METHOD

This method is essentially the same as the Coat and Heat Method described above, except that the surface of the skin is not cleaned after the carbon-oil suspension is applied and massaged into the hair ducts. During the irradiation step, the skin surface appears as shown in cross-section in FIG. 2B, rather than as shown in 2C. In this case, the carbon-oil suspension serves as a shield for the skin surface, permitting higher laser doses with no significant injury to the epidermis and dermis of the skin. Preliminary tests indicate that this is a very effective and safe method of hair removal. As the outermost surface of the skin is a very good insulator, substantial heat is prevented from transferring to the lower layers of the skin, and any significant damage to the skin is prevented.

ORAL AND INTRAVENOUS CONTAMINATION OF HAIR OF TISSUE

It is also possible to contaminate the hair or tissue feeding the hair by administering the contaminant orally or intravenously. A preferred method for oral contamination is as follows:

A solution of disodium fluorescein of 2–5% concentration is given orally. Within about 3 to 72 hours, a significant portion of the disodium fluorescein will be concentrated in the body hair of the patient. Sections of the skin containing the hair to be removed are irradiated with a laser pulsed at a wavelength matched to NaFl. Preferred laser sources are HeCd (441 nm), Nd:YAG (1,064 nm) frequency shifted to about 500 nm, and Er:Glass (1.54 $\mu$s;) tripled to 513 nm. Other sources with wavelengths from about 370 nm to 520 nm would be satisfactory. Preferred power levels are between about 5 to 15 J/cm$^2$, depending on hair depth, type of skin, metabolism of disodium fluorescein, etc. Preferred pulse duration is 1 $\mu$s, or less.

OTHER CONTAMINANT-LASER COMBINATIONS

There are many other chemicals that can be used in either the stain method or the photochemical method. Some of these are listed in Table 3 along with a corresponding laser recommended for the illumination.

OTHER EMBODIMENTS

It is very important for all of these embodiments and in other embodiments that will be apparent to persons skilled in the art that the light absorbing substances have a very high absorption coefficient at wavelengths that pass readily through the surface of the human skin. An illumination source is matched to this wavelength. The substance used can be one with a high resonance peak at the wavelength, or it can be one with a high broad absorption coefficient over a wide band containing the illumination wavelength. The important thing is to use a light of a wavelength that diffuses through the skin and has a relatively low absorption in the skin, and to use an absorber for contaminating the hair that will provide very high absorption of the light. Persons skilled in the art will recognize that certain wavelengths will be preferred for light skinned persons and other wavelengths may be preferred for dark skinned persons. The preferred beam size is about 1 square centimeter, but could be as large as about 5 square centimeters.

TABLE 3

Dyes and matching laser

| DYE | LASER |
|---|---|
| Hematoporphyrin derivatives | Argon Dye (630 nm) |
| Indocyanine Green | Diode Laser (785 nm) |
| Microcyanine | Cooper Vapor (540) |
| Photophrin II | Argon Dye (630) |
| Chlorin -E6 | Dye (660) |
| Chlorophyll derivatives | Argon Dye (630) |
| Black Ink | Ruby Laser (694) |
| Any of the above dyes | Tunable titanium-sapphire |

While the above description contains many specifications, these are not intended as limitations on the scope of the invention, but merely as exemplifications of embodiments thereof. Those skilled in the art will envision many other possible variations that are within the scope of the claims. Accordingly the reader is requested to determine the scope of the invention by the appended claims and their legal equivalents, and not by the examples which have been given.

I claim:

1. An apparatus useful for inhibiting hair growth in a section of skin having a plurality of hairs growing in hair ducts from follicles including:
    (a) a light-absorbing contaminant for infiltrating into the hair ducts; and
    (b) an illumination source in spaced apart relation to the contaminant infiltrated into the hair ducts for illuminating a surface of the section of skin and the contaminant, when infiltrated into the hair ducts, with a light, thereby causing a reaction that damages the follicles and/or skin tissue surrounding the follicles to inhibit hair growth.

2. The apparatus of claim 1 wherein the illumination source is a Nd:YAG laser.

3. The apparatus of claim 2 wherein the laser has a wavelength of about 1064 nm.

4. The apparatus of claim 1 wherein the contaminant includes carbon particles.

5. The apparatus of claim 4 wherein the carbon particles are graphite particles.

6. The apparatus of claim 4 wherein the contaminant further includes an oil.

7. The apparatus of claim 6 wherein the contaminant is a suspension of the particles in the oil.

8. The apparatus of claim 4 wherein the particles have a size of about 10 nm to about 20 nm.

9. The apparatus of claim 1 wherein the contaminant includes carbon powder.

10. The apparatus of claim 1 wherein the contaminant includes a hair dye and the illumination source is a dye laser.

11. The apparatus of claim 10 wherein the laser has a wavelength of about 587 nm.

12. The apparatus of claim 1 wherein the illumination source is a $CO_2$ laser and the light has a wavelength of about 10.6 microns.

13. A hair growth inhibition apparatus useful for inhibiting hair growth in a section of skin having a plurality of hairs growing in hair ducts from follicles therein including:
    (a) a light-absorbing contaminant for applying to a surface of the section of skin so that some of the contaminant infiltrates into the hair ducts; and
    (b) an illumination source for illuminating the surface with a light absorbed by the contaminant and being in spaced apart relation to the contaminant when applied to the surface, such that the light penetrates the section of skin and is absorbed by the contaminant in the hair ducts so as to destroy the follicles and/or skin tissue surrounding the follicles to inhibit growth.

14. The apparatus of claim 13 the illumination source is a Nd:YAG laser.

15. The apparatus of claim 14 wherein the laser has a wavelength of about 1064 nm.

16. The apparatus of claim 13 wherein the contaminant includes carbon particles.

17. The apparatus of claim 16 wherein the carbon particles are graphite particles.

18. The apparatus of claim 17 wherein the contaminant further includes an oil.

19. The apparatus of claim 17 wherein the contaminant is a suspension of the particles in the oil.

20. The apparatus of claim 16 wherein said particles have a size of about 10 nm to about 20 nm.

21. The apparatus of claim 13 wherein the contaminant includes carbon powder.

22. The apparatus of claim 13 wherein the contaminant includes a hair dye and the illumination source is a dye laser.

23. The apparatus of claim 22 wherein the laser has a wavelength of about 587 nm.

24. The apparatus of claim 13 wherein the illumination source is a $CO_2$ laser and the light has a wavelength of about 10.6 microns.

* * * * *